United States Patent [19]

Schwartz

[11] 4,048,040

[45] Sept. 13, 1977

[54] CLINICAL TESTING APPARATUS

[76] Inventor: Henry D. Schwartz, Palo Alto, Calif.

[21] Appl. No.: 646,288

[22] Filed: Jan. 2, 1976

Related U.S. Application Data

[63] Continuation-in-part of Ser. No. 320,264, Jan. 2, 1973, Pat. No. 3,941,565, and Ser. No. 640,542, Dec. 15, 1975, Pat. No. 3,994,171.

[51] Int. Cl.² ............................................. G01N 27/46
[52] U.S. Cl. ............................ 204/195 R; 204/195 M; 23/253 R; 73/423 A
[58] Field of Search ................. 204/1 T, 1 A, 195 R, 204/195 G; 23/230 R, 253 R, 254 E, 255 E, 292, 259; 73/423 R, 423 A, 424

[56] References Cited

U.S. PATENT DOCUMENTS

| | | | |
|---|---|---|---|
| 1,990,768 | 2/1935 | Youden | 204/195 G |
| 2,563,062 | 8/1951 | Perley | 204/195 G |
| 2,879,141 | 3/1959 | Skeggs | 23/230 R |
| 3,074,699 | 1/1963 | Skeggs et al. | 23/292 |
| 3,429,785 | 2/1969 | Ross | 204/1 A |
| 3,649,504 | 3/1972 | Evans et al. | 204/195 R |
| 3,684,452 | 8/1972 | Bessman | 23/253 R |
| 3,941,565 | 3/1976 | Schwartz | 23/253 R |
| 3,994,171 | 11/1976 | Schwartz | 23/253 R |

Primary Examiner—T. Tung
Attorney, Agent, or Firm—Wolf, Greenfield & Sacks

[57] ABSTRACT

The testing apparatus is preferably for the measurement of ionized calcium and other ions in biologic fluids. The apparatus generally comprises a turntable that is incrementally operated, a cover overlying the turntable, a housing for supporting the turntable and cover and a plurality of sample cups carried by the turntable. At one area of the cover there is defined a probe station having means supporting a plurality of probes which sample the fluid in the cups and generate electrical signal responsive to sensed ions which signal may be a high impedance signal. The electrical signal is coupled preferably via a coaxial cable to a relay device and from thence to an electrometer external of the apparatus. The relay device and other electrical or conductive components are isolated from chassis ground to improve signal transmission. A special shield dome covers the turntable, cover and probe assembly and this shield dome is the only part above the housing that is grounded. The dome has a lower position resting on the housing top and an upper position which permits access to the turntable. The dome is transparent as are the individual probes.

16 Claims, 4 Drawing Figures

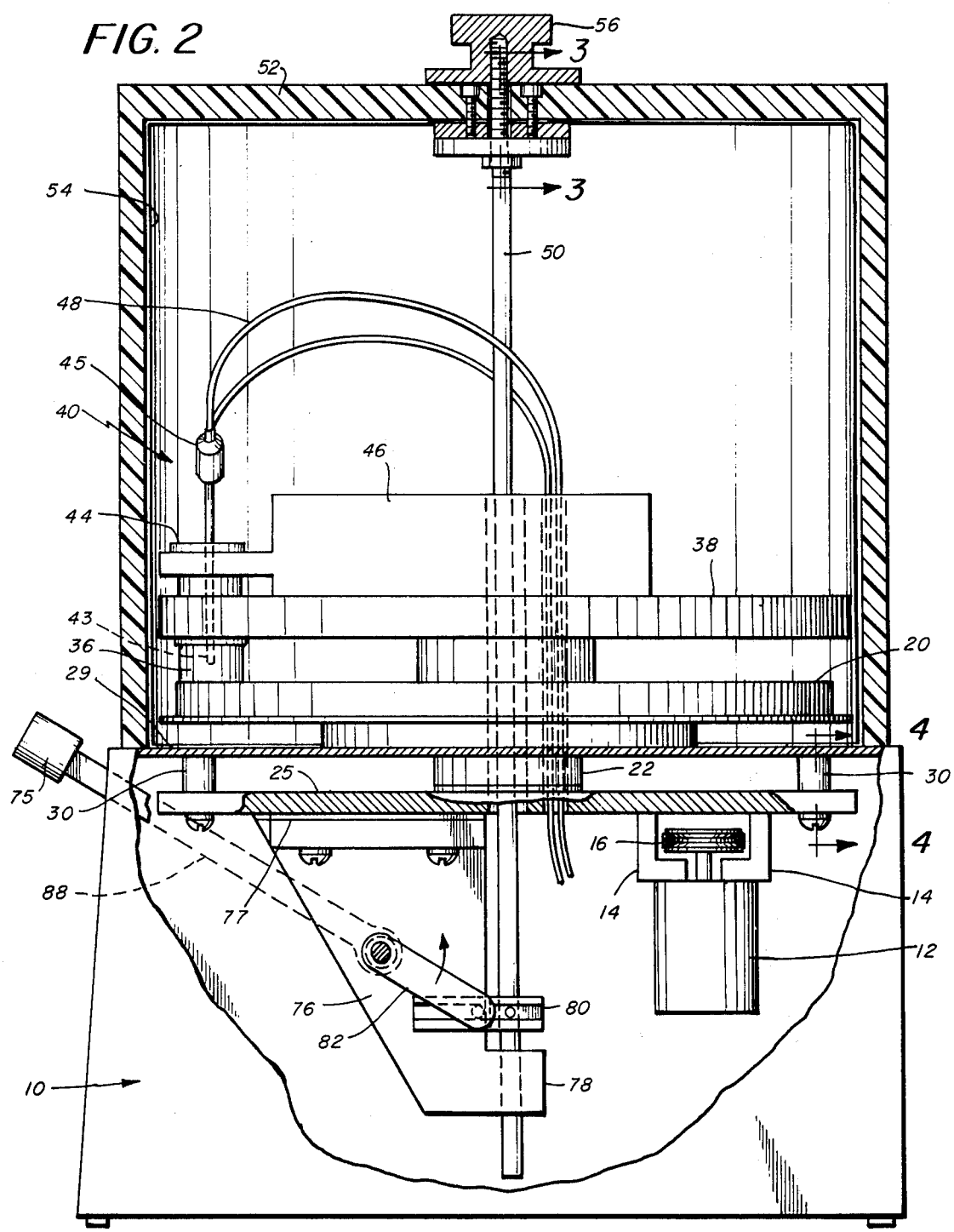
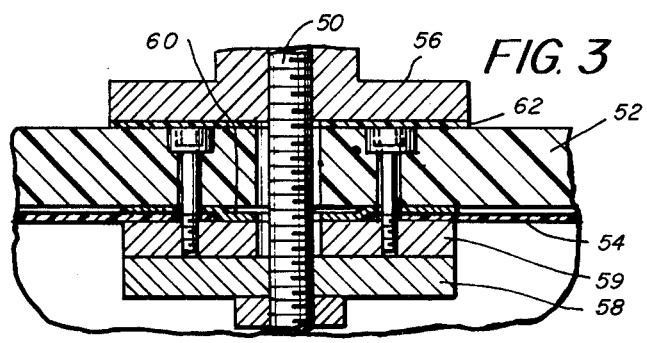
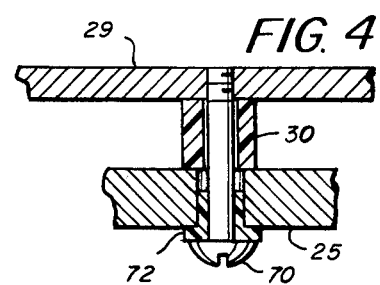

CLINICAL TESTING APPARATUS

RELATED APPLICATIONS

This is a continuation-in-part of applicant's copending applications Ser. Nos. 320,264 filed Jan. 2, 1973 and entitled CLINICAL TESTING MEANS AND METHOD, now U.S. Pat. No. 3,941,565, and application Ser. No. 640,542 filed Dec. 15, 1975 and entitled CLINICAL TESTING APPARATUS, now U.S. Pat. No. 3,994,171.

BACKGROUND AND SUMMARY OF THE INVENTION

The present invention relates in general to a clinical testing apparatus. More particularly, this invention pertains to a testing apparatus for making multiple sample clinical determinations of ionized calcium concentrations or other ions in body fluids. The aspects of this invention pertain primarily to some of the electrical phenomenon associated with the clinical testing apparatus of this invention.

U.S. Pat. No. 3,429,785 shows one probe arrangement for sampling ions in body fluids. One of the problems that is encountered is that the signals that are generated are extremely high impedance signals and thus it is difficult to handle these signals. Furthermore, it has been found that in existing machines that it is difficult to reject spurious electrical signals that may occur and interfere with the sampling operation. In these prior art machines it has been found that it is desirable to provide a shield which is attached to the electrode or probe. This shield may be in the form of a metallic paint or a metallic impregnated material which is fastened to the electrode. However, the presence of this shield prevents one from easily ascertaining the contents of the fluid contained within the probe. In an alternate arrangement in the prior art, a preamplifier is connected directly at the probe to amplify the signal and thereby supposedly lessen the chance of electrical interference. However, the addition of electrical components at the probe station provides a very cumbersome arrangement and makes it very difficult to use more than one probe at the probe station.

Accordingly, one object of the present invention is to provide a probe or electrode structure that is not necessarily provided with a shielding about the probe itself and that does not require the use of preamplifiers at the probe.

Another object of the present invention is to provide a probe that is constructed primarily of a transparent material such as glass so that the liquid level in the probe can be easily monitored.

It has been found in accordance with the present invention that, rather than shielding at the probe, a relatively large shield is provided which totally surrounds the probe station and also the turntable and cups and preferably all of the structure contained above the top wall of the housing. This shield is in the form of a dome which may be of cylindrical shape and may be constructed of a plastic material such as plexiglass which either has a relatively thin layer of conductive material evaporated on the inside surface thereof or has a thin membrane affixed inside thereof which membrane has a thin conductive layer deposited thereon. This conductive layer may be a gold layer but the layer is thin enough so that viewing is readily possible through the shield.

It has been further found in accordance with the invention that it is preferred that many of the electrical components contained within the housing and including also the turntable and cover external to the housing be electrically isolated from ground. In many of the prior art designs an attempt is made to ground many of these components and it has been found that this may lead to certain electrical difficulties. For example, if some of the liquid sample that is loaded into the cup is splashed onto the underside of the metal cover a liquid bridge may occur between the cover and the solution and if the cover were grounded there may be electrical interference that is created. In accordance with the teachings of the present invention, however, the cover is isolated. Futhermore, the relay device, for example, is also floating and isolated from ground.

In accordance with the present invention another important feature that has been discovered is that because of the unshielded metal especially within the housing, there may develop a static charge. To overcome this problem high quality capacitors have been used. For example, the entire cover and plenum metal assembly above the top of the chassis is connected by a high quality capacitor to ground and the relay device within the housing which is floating is also connected by a high quality capacitor to ground.

In accordance with the present invention it is also taught that the electrostatic shield in the form of the rather large dome that surrounds the turntable and cover, be movable between two positions by means of a handle on the housing. In one position of the handle the shield rests upon the top of the housing and forms an enclosed shield about the components outside of the housing. In order to load samples onto the turntable the handle is moved to a second position causing a lifting of the shield, permitting sufficient access to the turntable to permit the samples to be loaded thereon.

It has been mentioned that in accordance with the invention many of the components are maintained in a floating state. However, a ground wire is provided to the shield. This ground wire is coupled through the center support of the shield and is conductively coupled to the membrane or metallic layer within the dome of the shield.

BRIEF DESCRIPTION OF THE DRAWINGS

Numerous other objects, features and advantages of the invention should now become apparent upon a reading of the following detailed description taken in conjunction with the accompanying drawings, in which:

FIG. 2 is a side elevational view partially in cross-section and with the housing partially cut away to expose the inside of the housing;

FIG. 3 is a cross-sectional view showing a portion of the shield somewhat enlarged; and FIG. 4 is a cross-sectional view taken along line 4—4 of FIG. 2.

DETAILED DESCRIPTION

Figure 1:
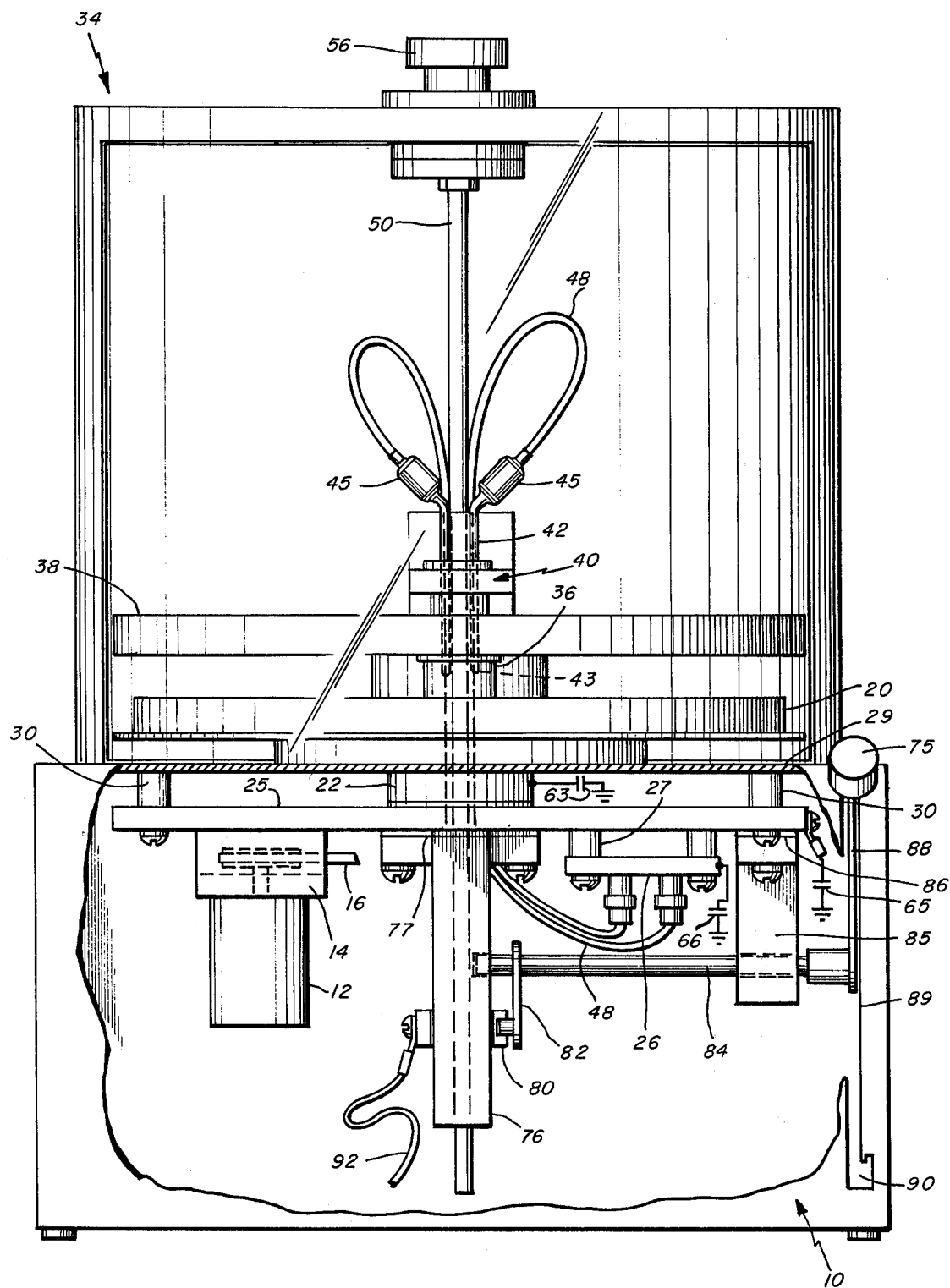
FIG. 1 is a front elevational view of the apparatus of this invention with the front of the housing partially cut away to expose the internal components.

Referring now to the drawings, there is shown a housing 10 in the form of a metal chassis. There are many electrical components contained within the housing 10, many of which are not shown in the drawings so as not to obscure the principles of the present invention. The internal portion of the housing is shown in a somewhat schematic fashion. For example, on the front panel of the housing which is shown cut away in FIG. 1, there may be provided temperature indicating devices, control switches and a switch array for selecting one of the plurality of probes for testing.

There is schematically shown within the housing a motor 12 supported from a pair of Teflon blocks 14. The output from motor 12 couples to a gear plate 16 only a fragment of which is shown in FIG. 1. This plate 16 appropriately couples to the turntable 20 disposed above the housing 10 for selectively operating the turntable 20. The turntable 20 is supported on a selectively driven hub 22. The Teflon blocks 14 support the motor 12 from a common support plate 25. This support plate 25 also supports the relay device 26. Again, Teflon blocks 27 are provided for supporting the relay device 26 from the support plate 25. The plate 25 is in turn supported from the bottom side of the top wall 29 of the housing by means of insulating posts 30 which may also be constructed of a Teflon material.

The housing 10, including the top wall 29, is preferably constructed of a metal material but the hub 22 which extends through the housing is insulated from the housing as is the plate 25. Thus, all of the parts shown within the dome 34 are floating and insulated from the chassis. These parts include the turntable 20 which receives a plurality of sample cups or containers 36, the overlying cover 38 and the probe assembly 40. Reference is made herein to my copending application Ser. No. 640,542 which shows more detail of the cover and turntable structure.

The probe assembly 40 comprises a plurality of probes 42, a probe holder 44 for a plurality of probes, and a support mechanism 46 which is selectively operated in conjunction with the operation of the turntable to withdraw the probes from the cups while the turntable is rotating. When the turntable has moved to its next station then the mechanism 46 permits the probe assembly 40 to move downwardly so that the probe again enters the next cup 36.

The probes 42 or, as they are sometimes referred to, electrodes, may be of the type shown in U.S. Pat. No. 3,429,785 wherein the sampling is done without having to withdraw the fluid from the cup 36. The probes 42 are each made preferably entirely of a clear transparent glass. The calcium or other ion selected material is packed in the very tip 43 of the probe. An internal filling solution, which in the case of a calcium electrode would be calcium chloride, is placed in each of the chambers defined by the probe. The shaft of the glass probe or electrode is approximately ⅛ inch in diameter but may even be narrower and has near its upper end a flared section defining a cylindrical chamber that may be approximately ¼ inch in diameter. This enlarged chamber permits an adequate amount of calcium chloride filling solution to be contained within the probe. The probe is preferably provided with a small loading porthole near the top end of the chamber for replenishing the calcium chloride liquid. The probe is preferably bent as shown at an angle of approximately 30° just before the enlarged portion of the probe thereby permitting several of these electrodes or probes to be arranged physically close to one another.

A silver conductor wire continuous electrically with the cable 48 extends from the top end of each probe. This wire is preferably formed with a silver/silver chloride tip and is supported in a Teflon dowel which may be pressed into an electrical coaxial fitting at the end of the probe. The end of the Teflon dowel press fits into or around the top of the electrode glass shell which is of the same diameter as the bottom section of the probe or approximately ⅛ inch in diameter. The silver wire is of sufficient length to extend into the internal filling solution in the glass probe.

It is noted that in this preferred construction there is no electronic shielding attached to the electrode itself. Many times problems occur in that air bubbles have a tendency to get trapped in the probe and frequently interrupt the continuity between the calcium selective material at the tip and the wire within the probe. With the construction of the present invention wherein the probe is made of a clear transparent material, there is complete visibility afforded such that bubbles can readily be disloged at the time of initially loading the electrode. Further, the probe can be periodically checked to see if bubbles develop during use. Also, because the probe is transparent the filling level of the internal filling solution can be periodically checked to see that the level is maintained within the chamber 45 of the probe. It is also preferred that the holder 44 be made of a transparent material so that the actions at the probe station can be readily ascertained.

As previously mentioned, in the past attempts have been made to shield the probe or electrode itself by using metallic conductive materials. However, it has been found that electrical interference may develop. Part of this interference is believed to stem from the fact that a ground is provided to the shield which may cause a polarization of the electrodes destroying their slope effectiveness and further causing instability in readings and interference between different probes. It has been found in accordance with this invention that it is an advantage to have the sensing material at the very tip of the probe. In this way the probe samples the specimen being measured directly at the surface and one can readily observe whether there is any deterioration in the material at the sensing tip, or whether, for example, it has become coated with debris or fibrin as may occur with blood, for example, in which the electrodes can easily be cleaned by wiping with a moist tissue.

In accordance with the present invention as can be seen in the drawings, the electrostatic shield 34 is in the form of a cylindrical shaped dome that surrounds the entire probe assembly, cover and turntable. The dome is entirely supported at its center by the elongated support rod 50 which also functions as a conductor but is preferably insulated on its outer surface along at least a majority of its length. The rod 50 may be anodized to provide this outer surface insulation. The shield 34 comprises a cylindrical shaped dome 52 which may be constructed of a transparent plastic material such as plexiglass. A membrane 54 is suitably affixed within the dome 52 such as even by being taped at its lower edge. The membrane 54 has a thin layer of a conductive material such as gold deposited on the side facing the dome 52. The elongated rod 50 has a threaded top end which receives a knob 56 which secures the shield 34 to the rod 50.

The enlarged cross-sectional view of FIG. 3 shows the details at the center axis of the shield. The rod 50 may be insulated as previously mentioned but the flange 58 and its associated lip 59 are constructed of metal and conductively connect to the rod 50. On the lip 59 is disposed a metal fork 60 which connects and contacts the outer surface of the membrane 54. The membrane 54 may be constructed of a clear mylar material having a thin layer of gold deposited on its outer surface. With the arrangement shown in FIG. 3 the metal fork contacts this thin layer and provides the necessary ground or other voltage continuity to the thin gold layer which actually forms the metallic shielding material. FIG. 3 also shows the dome 52 and a portion of the knob 56 which is preferably insulated from the dome by means of a Teflon tape 62.

The coaxial cables or wires 48 which connect from the electrode wire couple down through passages in the device, such as passages through the mechanism 46 and the hub 22 to a relay device 26 which is preferably a coaxial relay. A coaxial cable relay system is highly effective for coupling high impedance signals. As previously mentioned, the device 26 is completely floating and isolated from ground. The single output lead coupling from the device 26 couples to the back of the housing and from there is connected externally to an electrometer.

It has been found that because unshielded pieces of metal may develop a static charge and actually function as at least one plate of a capacitor, electrical interferences may develop. It is has been found that by connecting a capacitor from these metal bodies to ground, electrical interference is effectively reduced or eliminated. Thus, the entire cover and in fact all of the parts above the housing 10 may be connected by way of a capacitor 63 to ground, as shown in FIG. 1. Similarly, the support plate 25 may be coupled by way of a high quality capacitor 65 to ground. Further, the support plate for the device 26 may also be coupled by way of a capacitor 66 to ground. It is realized, however, that even though these pieces of metal are connected by a high quality capacitor to ground that those pieces of metal are not in the conventional sense "grounded." Thus if a person in loading the cups with a liquid sample should spill some of the liquid on the underside of the metal cover and create a liquid bridge between the cover and the solution, no ground impulse is transmitted to the cup and there would not be any interference with the electrical stability.

FIG. 4 shows one detail of a typical insulating support. FIG. 4 is a view taken along line 4—4 of FIG. 2 showing the insulating post 30 disposed between the top wall 29 of the housing and the support plate 25. FIG. 4 shows a bolt 70 passing through a hole in the plate 25 but insulated from the plate 25 by an insulating washer 72 which extends through the hole. The bolt threadedly engages with a threaded hole in the plate 29. With this arangement the plate 25 is completely isolated from the grounded chassis.

In accordance with the present invention the shield 34 preferably is movable between two positions. One position is the one shown in FIG. 1 wherein the shield rests upon the top surface of the wall 29 of the housing. It is noted that the control knob 75 is in its upper position corresponding to that position of the shield. When the control knob 75 is moved to its lower position this causes the shield 34 to move upwardly to its upper position. In this upper position there is free access to the turntable 20 permitting samples to be installed on the turntable or removed therefrom.

The lower end of the rod 50 is supported by means of bracket 76. Bracket 76 is supported from plate 25 and an insulating washer 77 is provided between the plate 25 and the bracket 76. The lower end 78 of the bracket has a passageway for accommodating the rod 50. A slide bar 80 is secured to the rod 50 and a pivot arm 82 is secured to the slide bar 80. The shaft 84 when caused to rotate, pivots the arm 82 thereby raising or lowering the rod 50. The rod 84 is supported by a support block 85 supported from plate 25 but having an insulating washer 86 between the block 85 and the plate 25. The knob 75 connects to an actuating handle 88 which, when pivoted downwardly, causes rotation or the rod 84 which in turn causes the slide bar 80 to move upwardly thereby raising the rod 50 and the entire shield 34. The handle 88 slides in a slot 89 and in the front wall of the housing. This slot terminates at its bottom end in a reverse turn 90. When the knob 75 is moved downwardly the handle 88 may engage in this reverse turn section of the slot and be held in that position permitting access to the turntable above the housing. A ground lead 92 is shown appropriately connecting to this slide bar 80. Thus, the bracket 76 which is grounded by this ground connection is not coupled to the plate 25. Furthermore, the arm 82 is connected to the slide bar 80 so that there is a ground coupled to the rod 84 by way of arm 82, and in turn to the handle 88 and associated knob 75. The block 85 has an insulating washer for isolating the block 85, which is not grounded, from the grounded rod 84.

What is claimed is:

1. In a testing apparatus for measuring ions in body fluid which apparatus comprises a rotatable turntable with a plurality of containers mounted thereon, a cover overlying the turntable and contacting the container mouths, and a chassis supporting the turntable and cover, the improvement comprising;
   an electrostatic shield disposed above the chassis surrounding the turntable and cover and comprising a transparent member having a transparent conductive film layer on the outside thereof,
   means for supporting the shield from the chassis including an elongated operating rod extending centrally of said shield from the shield, said chassis having a passage for accommodating the rod,
   and means mounted from the chassis for lifting the shield by lifting the operating rod whereby the shield has at least two stationary positions one of which permits access to the turntable.

2. In a testing apparatus as set forth in claim 1 including means for coupling a ground or other reference level signal to the conductive film layer of the shield.

3. In a testing apparatus as set forth in claim 1 and further comprising means for grounding the rod and means for conductively coupling the top end of the rod to the thin conductive film layer.

4. In a testing apparatus as set forth in claim 3 including a knob engageable with the rod for securing the shield to the rod.

5. In a testing apparatus as set forth in claim 1 including a plurality of probes each formed of a transparent material and means for commonly supporting the probes.

6. In a testing apparatus as set forth in claim 1 including at least one electrical or conductive component and means for insulatedly supporting the component from the chassis.

7. A testing apparatus as set forth in claim 1 including means for locking the shield in its upper position.

8. Testing apparatus as set forth in claim 1 wherein said means for supporting includes conductive means electrically connecting said operating rod and said conductive film layer.

9. In a testing apparatus for measuring ions in body fluid which apparatus includes a rotatable turntable with a plurality of containers mounted thereon, a cover overlying the turntable and contacting the container mouths, and a chassis supporting the turntable and cover, the improvement comprising;

an electrostatic shield means having an open bottom disposed over the chassis to thereby enclose the turntable and cover, said electrostatic shield means comprising a transparent dome, a membrane member having a transparent thin conductive film layer on the outside thereof, and means securing the membrane member within the dome, means coupling the shield means to the chassis for supporting the shield means from the chassis, and means associated with the chassis for lifting the shield means by lifting the supporting means whereby the shield means has at least two stationary positions one of which permits access to the turntable.

10. Testing apparatus as set forth in claim 9 wherein said means for supporting includes an elongated rod for centrally supporting the shield means.

11. Testing apparatus as set forth in claim 9 including means in the chassis for holding the bottom end of the shield support means.

12. Testing apparatus as set forth in claim 11 including means for grounding said shield support means.

13. Testing apparatus as set forth in claim 9 including means for locking said means for lifting in an elevated position of said shield means.

14. Testing apparatus as set forth in claim 9 wherein said means for supporting includes an elongated rod and said means for lifting includes an actuating handle coupled to the rod and having an end extending from the chassis and movable to at least two fixed positions.

15. In a testing apparatus for measuring ions in body fluid which apparatus includes a rotatable turntable with a plurality of containers mounted thereon, a cover overlying the turntable and contacting the container mouths, and a chassis supporting the turntable and cover, the improvement comprising;

an electrostatic shield means having an open bottom disposed over the chassis to thereby enclose the turntable and cover, said electrostatic shield means comprising a transparent member having a transparent conductive film layer on the outside thereof, means coupling the shield means to the chassis for supporting the shield means from the chassis, and means associated with the chassis for lifting the shield means vertically by lifting the means for supporting whereby the shield means has at least two stationary positions one of which permits access to the turntable.

16. Testing apparatus as set forth in claim 15 wherein said chassis has a top wall upon which the shield means rests and further comprising locking means for maintaining the shield means in its elevated position with the shield means lifted vertically only a sufficient distance above the top wall to expose the turntable.

* * * * *